(12) United States Patent
Sun et al.

(10) Patent No.: US 8,779,209 B2
(45) Date of Patent: Jul. 15, 2014

(54) METHOD FOR SALTING-OUT EXTRACTION OF ACETONE AND BUTANOL FROM A FERMENTATION BROTH

(75) Inventors: Yaqin Sun, Dalian (CN); Zhigang Li, Dalian (CN); Zhilong Xiu, Dalian (CN)

(73) Assignee: Dalian University of Technology, Dalian, Liaoning (CN)

( * ) Notice: Subject to any disclaimer, the term of this patent is extended or adjusted under 35 U.S.C. 154(b) by 0 days.

(21) Appl. No.: 13/812,133

(22) PCT Filed: Dec. 27, 2010

(86) PCT No.: PCT/CN2010/080286
§ 371 (c)(1),
(2), (4) Date: Mar. 28, 2013

(87) PCT Pub. No.: WO2012/013004
PCT Pub. Date: Feb. 2, 2012

(65) Prior Publication Data
US 2013/0190536 A1    Jul. 25, 2013

(30) Foreign Application Priority Data
Jul. 27, 2010   (CN) .......................... 2010 1 0238187

(51) Int. Cl.
*C07C 45/86* (2006.01)
*C07C 27/34* (2006.01)
(52) U.S. Cl.
USPC .......................................... 568/411; 568/913
(58) Field of Classification Search
USPC .................................................. 568/411, 913
See application file for complete search history.

(56) References Cited

U.S. PATENT DOCUMENTS 5,755,967 A    5/1998  Meagher et al.

FOREIGN PATENT DOCUMENTS

| CN | 101012152 A | 8/2007 |
|---|---|---|
| CN | 101898945 A | 12/2010 |
| SU | 1268559 A1 | 11/1986 |

OTHER PUBLICATIONS

Chen, "Production technology for acetone and butanol fermentation," Chapter 5. Distillation, Chemical Industry Press, 1991, 4 pages. (with English Translation).
Durre, "New insights and novel developments in clostridial acetone/butanol/isopropanol fermentation," Appl Microbiol Biotechnol 49: 639-648, 1998.
Ezeji et al., "Bioproduction of butanol from biomass: from genes to bioreactors," Current Opinion in Biotechnology 18: 220-227, 2007.
Gao et al., "Extraction System of n-Propanol—NaCl—H2O for Rh (III)—SnCl2—2—Mercaptobenzothiazole and Its Application," Fenxi Ceshi Xuebao (Journal of Instrumental Analysis) 21(3): 75-77, May 2002, 9 pages. (with English Translation).
Hu et al., "Separation of Butanol-Acetone-Water System Using Repulsive Extraction," Journal of South China University of Technology (Natural Science Edition) 31(12): 58-62, Dec. 2003, 15 pages. (with English Translation).
Hu et al., "Preliminary study on coupling between biodiesels and acetone-butanol fermentation," Chinese Journal of Bioprocess Engineering, pp. 27-32, Feb. 2007, 17 pages. (with English Translation).
International Search Report, dated Mar. 31, 2011, for International Application No. PCT/CN2010/080286, 5 pages.
Jiang et al., "Aqueous two-phase extraction of 2,3-butanediol from fermentation broths using an ethanol/phosphate system," Process Biochemistry 44: 112-117, 2009.
Li et al., "Extraction Separation of Mercury in NaCl-Kl-Propanol System," Chinese Journal of Applied Chemistry 18(3): 241-243, Mar. 2001, 9 pages. (with English Translation).
Li et al., "Aqueous two-phase extraction of 1,3-propanediol from glycerol-based fermentation broths," Separation and Purification Technology 66: 472-478, 2009.
Louwrier, "Model phase separations of proteins using aqueous/ethanol components," Biotechnology Techniques 12(5): 363-365, May 1998.
Luo et al., "Separation and concentration of butanol from acetone, butanol, ethanol mixed solution by pervaporation," Chemical Engineering (China) 38(2): 43-46, Feb. 2010, 15 pages. (with English Translation).
Qureshi et al., "Continuous Production of Acetone-Butanol-Ethanol Using Immobilized Cells of Clostridium acetobutylicum and Integration with Product Removal by Liquid-Liquid Extraction," Journal of Fermentation and Bioengineering 80(2): 185-189, 1995.
Schugerl, "Integrated processing of biotechnology products," Biotechnology Advances 18: 581-599, 2000.
Sun et al., "Aqueous two-phase extraction of 2,3-butanediol from fermentation broths by isopropanol/ammonium sulfate system," Biotechnol Lett 31: 371-376, 2009.
Written Opinion, dated Mar. 31, 2011, for International Application No. PCT/CN2010/080286, 5 pages.
Zhang et al., "Aqueous Two-phase Extraction of 2,3-Butanediol from Fermentation Broth," The Chinese Journal of Process Engineering 8(5): 897-900. Oct. 2008, 14 pages. (with English Translation).

*Primary Examiner* — Sikarl Witherspoon
(74) *Attorney, Agent, or Firm* — Seed IP Law Group PLLC

(57) ABSTRACT

The present invention provided a method for salting-out extraction of acetone and butanol from a fermentation broth, characterized in that one type, or two or more types of salts and one type, or two or more types of extractants are added to an acetone-butanol-ethanol (ABE) fermentation broth, in which the salt saturation achieves 10%~100%; and the volume ratio of the fermentation broth containing salts to the extractants is 1:0.1~1:5. The mixture is allowed to stand until phase separation is formed. The top phase is a solvent phase or extraction phase enriched with acetone and butanol whereas the bottom phase is a salt-enriched phase or raffinate phase. This method involves many advantages, such as the simplified operation procedure, accelerated separation process and low separation cost, and therefore becomes a promising method of separating acetone and butanol in industrial application.

8 Claims, No Drawings

METHOD FOR SALTING-OUT EXTRACTION OF ACETONE AND BUTANOL FROM A FERMENTATION BROTH

FIELD OF THE INVENTION

The present invention relates generally to the field of bioengineering technology, involving the separation techniques applied to microbial fermentation broths. More particularly, it concerns a method for salting-out extraction of acetone and butanol from a fermentation broth.

BACKGROUND OF THE INVENTION

Acetone and butanol are excellent organic solvents and important chemical materials. Butanol can be used as a solvent for paint and surface coating materials, as well as for the production of plastic and rubber products. Moreover, butanol can also be utilized to produce chemical products such as butyl acetate, butyl acrylate, butyraldehyde, butyric acid, butyl amine and butyl lactate, etc. Butanol is an attractive liquid fuel, other than ethanol. Acetone is mainly used as the solvent for producing cellulose acetate films, plastics and coating materials. Besides being used as a solvent, acetone can also be mainly used to produce chemical products, such as methyl methacrylate (MMA), bisphenol A, aldol condensation substances, and the like. Acetone-butanol-ethanol (ABE) fermentation is a traditional large-scale fermentation process, which, as merely inferior to ethanol fermentation, has been the second most important fermentation process in the world. Since the early stage of PRC, corn flour has been used for the industrial production of ABE fermentation, so that a reliable fermentation technique had been built up. Then the ABE fermentation technique declined because of the development of petrochemical industry. However, due to the increasing risks in environmental issues such as the exhaustion of petrochemical resources, greenhouse effects and the like, production of chemical materials and energy substances from renewable resources has attracted more and more attention. Therefore, ABE fermentation, once again, exhibits its advantages in this competition. Nevertheless, the total concentration of the solvents obtained using the current ABE fermentation process is very low. In general, the total concentration of the solvents (acetone, butanol and ethanol) ranges approximately from 15 to 20 g/L. As a result, the cost for extracting and separating the solvents is very high, which restricts the application of acetone and butanol as well as the production of ABE fermentation. Ever since the production of acetone and butanol by fermentation became possible, researchers had been working intensively to develop a convenient, low-cost and efficient separation method.

The traditional process for the purification of acetone-butanol-ethanol involves the following steps. First, a fermentation broth is distilled and concentrated by passing through a simple distillation column, so that the solid impurities and partial water are removed from the fermentation broth and 4% of ethanol, 10% of acetone, 26% of n-butanol and 60% of water are obtained. Then distillation is carried out again to further purify the solvents, i.e. ethanol, acetone and n-butanol. A huge amount of energy is consumed in this process. In fact, about 18 tons of steam is required to produce 1 ton of solvents in industry (Chen, T. *Chemical Industry Press*, 1991). Especially, approximately 10 tons of steam is consumed in the separation process, which accounts for 60% of total energy consumption. Presently, the major technologies used to extract and separate acetone and butanol from fermentation broths include adsorption, gas stripping, liquid-liquid extraction, pervaporation, repulsive extraction (salting-out) and so on. In general three different types of materials including diatomite, activated carbon and polyvinylpyrrolidone were used as absorbents in adsorption technology. Meagher et al. (U.S. Pat. No. 5,755,967[P], 1998) utilized diatomite to absorb acetone and butanol from the fermentation broths, and found that that diatomite had a higher ability for absorbing butanol and acetone. Unfortunately, desorption was not investigated in this study. Compared with other methods, adsorption technology has some disadvantages, including the higher cost, complicated manipulation, low selectivity, high energy consumption and liableness to the contamination caused by fermentation broths (*Biotechnology Advances*, 2000, 18(7): 581-599). Coupling between gas stripping and ABE fermentation can increase the fermentation yield and substrate utilization. However, this technology relies on many factors, such as the recovery speed of carried gas, bubble size, antifoaming agents and so on, and thus involves a complicated operation procedure. For liquid-liquid extraction, most researches concerning the extractants focused on oleyl alcohol (*Current Opinion in Biotechnology*, 2007, 18: 220-227), benzyl benzoate, dibutyl phthalate (*Journal of Fermentation and Bioengineering*, 1995, 2(80): 185-189), biodiesel (*Chinese Journal of Bioprocess Engineering*, 2007, 5(1): 27-33) and so on. However, liquid-liquid extraction also has some disadvantages, such as its low distribution coefficient, low recovery yield, occurrence of emulsification and so on. Luo et al. utilized pervaporation membrane separation technology (*Chemical Engineering* (China), 2010, 38(2): 43-46) to study the separation of ABE system. The separation was started from a simulated fermentation broth. The results indicated that pervaporation technology can be used as an efficient method for the separation and concentration of butanol from the ABE system, but is not suitable for efficiently separating acetone from the ABE system. Moreover, pervaporation strongly relies on the properties of the membrane materials. The separation performance and flux depend on the properties of the membrane to a great extent. The short lifetime of the membrane restricts the application of this technique to some extent (*Appl. Microbiol. Biotechnol.*, 1998, 49: 639-648). Hu et al. utilized repulsive extraction to study the effect of various salts on the separation of acetone and butanol from a simulated ABE fermentation broth. The results indicated that utilization of a composite extractant can greatly increase the distribution coefficient and selection coefficient of butanol and acetone in the two phases, and thus, to some extent, accomplishes the separation and concentration of butanol and acetone (*Journal of South China University of Technology*, 2003, 31:58-62).

Recently, while investigating solvent crystallization, some researchers found that at a proper temperature, liquid-liquid phase separation, rather than salt crystallization, may occur if the concentrations of the inorganic salts, organic solvents and water are appropriate in the system. Moreover, if hydrophilic low-molecular substances, such as methanol, ethanol, acetone and so on, were used as the organic solvents, a novel aqueous two-phase extraction system could be formed. Compared with the traditional aqueous two-phase system composed of high molecular polymer and salt, this novel aqueous two-phase system has many advantages, for example, the phase separation is clearer; the cost is lower; and no polymer having a high viscosity and disposal difficulties exists in the extraction phase. Although the researches focusing on this field has just started in the whole world, its excellent separation performance has been noticed. For example, the dipotassium hydrogen phosphate/ethanol system was used by Louwrier to extract biomacromolecules, such as bovine serum albumin (BSA), α-casein, ribonuclease and so on (*Biotechnology Techniques*, 1998, 12 (5): 363-365). The acetone/sodium chloride system was utilized by Li and Gao et al. to extract metal complex and metal ion (*Chinese Journal of Applied Chemistry*, 2001, 18 (3): 241-243; *Journal of Instrumental Analysis*, 2002, 21 (3): 75-77). All of the above researches have achieved satisfying results. This novel aqueous two-phase system was also used to separate 1,3-propanediol and 2,3-butanediol from fermentation broths in our previous work. The separation of the target products from fermentation broths was accomplished effectively, and the separation effect was prominent (*The Chinese Journal of Process Engineering*, 2008, 8 (5): 888-900; *Process Biochemistry*, 2009, 44, 112-117; *Biotechnol. Lett*, 2009, 31 (3): 371-376; *Separation and Purification Technology*, 2009, 66: 472-478). In fact, salting-out effect not only benefits the extraction of hydrophilic organic solvents, but also improves the traditional organic extraction. The combination of salting-out and extraction forms a novel salting-out extraction (SOE) technology, and the novel aqueous two-phase extraction is one type of the SOE technology. Up to now, SOE systems have not been reported to be used in the separation of the acetone-butanol-water system. Compared with the traditional extraction using organic solvents, SOE technology has many advantages, including the high distribution coefficient, high recovery yield and low solvent consumption, etc. Compared with the traditional salting-out or repulsive extraction, SOE technology involves low salt consumption and low corrosiveness to equipments. Moreover, the inorganic and organic salts can be recycled and used for multistage salting-out extraction. Compared with the traditional aqueous two-phase PEG/inorganic salt system, SOE technology has advantages such as high distribution coefficient, rapid phase separation, easy recycle of solvents and products, low cost and so on. Compared with other separation methods, SOE technology also has some advantages, including its simple operation procedure, low energy consumption and high efficiency. Furthermore, SOE technology allows the separation of acetone and butanol directly from a fermentation broth, i.e. the step of solid-liquid separation is omitted.

SUMMARY OF THE INVENTION

The present invention provides a method for the separation of acetone and butanol from a fermentation broth using a salting-out extraction technique. This method overcomes the shortcomings, such as complicated procedures, low separation abilities, low total yields and high energy consumption found in the current separation processes.

The embodiments of the invention are shown as follows:

An ABE fermentation broth may be pretreated by flocculation, filtration, microfiltration or centrifugation, so as to remove bacteria and obtain a clear broth. It can also be an untreated original fermentation broth, or a concentrated original broth or clear broth. The concentration of acetone and butanol ranges from 4 g/L to 500 g/L. One type, or two or more types of salts are added to the above fermentation broth or clear broth. The added salts can be solid or concentrated salt solutions. The salt saturation achieves 10%~100% in the fermentation broth after addition of the salts. Then one type, or two or more types of extractants are added, and the volume ratio of the fermentation broth containing salts to the extractants is 1:0.1~1:5.

The inorganic salt can be selected from sodium carbonate, potassium carbonate, sodium chloride, lithium chloride, ammonium sulphate, sodium sulphate, dipotassium hydrogen phosphate, sodium hydrogen phosphate, potassium phosphate, sodium phosphate, potassium dihydrogen phosphate, or sodium dihydrogen phosphate, and so on.

The organic salt can be selected from sodium acetate, potassium acetate, sodium citrate, potassium citrate, sodium oxalate, or potassium oxalate, and so on.

The extractant can be selected from methanol, ethanol, acetone, n-propanol, isopropanol, n-butanol, isobutanol, ethylene glycol, ether, methyl acetate, or ethyl acetate, and so on.

The mixture obtained as above is allowed to stand until phase separation is formed. The top phase is solvent phase or extraction phase enriched with acetone and butanol whereas the bottom phase is a salt-enriched phase or raffinate phase. After the salting-out extraction, the fermentation broth containing bacteria forms a solid phase between the top and the bottom phases. The solid phase consists of cells, proteins, nucleic acids and polysaccharides, etc. Distillation and rectification are conducted for recovering solvents from the solvent phase or extraction phase, and crude acetone and butanol products and solid salts are also obtained. The concentrated salt solution obtained from the salt-enriched phase or raffinate phase by distillation can be recycled, or can be provided with the recovered organic solvent so that the salts can be crystallized out. For alkaline salts, $CO_2$ discharged from fermentation and separation processes can be passed into the salt-enriched phase which has been extracted, and reacts with an alkaline salt to generate an acid salt with a lower solubility. Then the resultant acid salt is precipitated, or recovered by filtration and centrifugation, or is subjected to solvent dilution crystallization by adding an organic solvent. The generated acid salt can be sodium bicarbonate, potassium bicarbonate, ammonium bicarbonate, potassium dihydrogen phosphate or sodium dihydrogen phosphate, etc. The generated acid salt, as a byproduct, can be utilized directly, or also can be used for the recovery of the concentrated $CO_2$ and alkaline salts by thermal decomposition, so that acetone and butanol can be produced by a fermentation process with reduced energy consumption and pollution emission.

The salting-out extraction may be conducted in a batch or continuous operation mode, and the multistage extraction mode can be applied in the system with a lower distribution coefficient.

This invention overcomes many shortcomings found in the current processes of extracting and separating acetone and butanol from a microbial fermentation broth. The advantages of this invention include the simplified operation procedure, accelerated separation process, lower costs and economic feasibility. More specifically, firstly, the salting-out extraction (SOE) systems consisting of single or complex extractants and inorganic/organic salts have excellent extraction effect for acetone and butanol, which resolves the low efficiency issue of the traditional extractants. The extractants can be selected from acetone, butanol, ethanol or a mixture thereof, which reduces the production cost. Secondly, the SOE system allows a fermentation broth to be processed directly and the step of separating bacteria is omitted. Meanwhile, most of the nucleic acids, proteins and polysaccharides can be removed from the fermentation broth. As a result, many problems, such as the higher energy consumption caused by ultrafiltration, membrane cleaning requirement and difficulties to recovering the plenty of acetone and butanol remained in the concentrated bacteria solution, etc. Thirdly, $CO_2$ can be recycled and its emission is reduced. By absorption of the $CO_2$ generated from the production process in the salt-enriched phase, not only inorganic salts, but also most $CO_2$ can be recovered, which overcomes the difficulty in recovering salts from the SOE system and solves the problem of large $CO_2$ emission in the production process.

DETAILED EMBODIMENTS

The detailed examples of the invention are described in detail by referring to the following technical solutions.

A simulated fermentation broth was obtained by dissolving butanol, acetone and ethanol (all in analytical grade) in water. The final concentrations of butanol, acetone and ethanol were 21.08 g/L, 10.17 g/L and 3.82 g/L, respectively.

A fermentation broth was obtained using glucose-based fed-batch fermentation by *Clostridium acetobutylicum* L7. The concentrations of butanol, acetone and ethanol were 13.51 g/L, 6.47 g/L and 2.15 g/L, respectively.

Example 1

Salting-Out Extraction of Butanol and Ethanol from the Simulated Fermentation Broth Using a $K_2HPO_4$/Acetone System $K_2HPO_4$ (2.5 g) was added to 5 g of the simulated fermentation broth. Then, after the salt was dissolved, 2.5 g acetone was added. The resultant mixture was mixed and then held. Two phases were formed. The volume of the top phase was 4.2 mL and the concentrations of butanol, acetone and ethanol were higher in the top phase. Contrarily, the concentration of the salt was higher in the bottom phase and the volume of the bottom phase was 4.3 mL. The distribution coefficients of butanol, acetone and ethanol were 391.84, 58.90 and 16.07, respectively. The recovery yields of butanol and ethanol were 99.74% and 94.01%, respectively.

Example 2

Salting-Out Extraction of Acetone and Butanol from the Simulated Fermentation Broth Using a $K_2HPO_4$/Ethanol System $K_2HPO_4$ (2.5 g) was added to 5 g of the simulated fermentation broth. Then, after the salt was dissolved, 2.5 g ethanol (95%) was added. The resultant mixture was mixed and then held. Two phases were formed. The volume of the top phase was 4.9 mL and the concentrations of butanol, acetone and ethanol were higher in the top phase. Contrarily, the concentration of the salt was higher in the bottom phase and the volume of the bottom phase was 4 mL. The distribution coefficients of butanol, acetone and ethanol were 25.03, 71.29 and 14.76, respectively. The recovery yields of butanol and acetone were 96.84% and 98.87%, respectively.

Example 3

Salting-Out Extraction of Butanol and Ethanol from the Simulated Fermentation Broth Using a $Na_2CO_3$/Acetone System $Na_2CO_3$ (1.5 g) was added to 6 g of the simulated fermentation broth. Then, after the salt was dissolved, 2.5 g acetone was added. The resultant mixture was mixed and then held. Two phases were formed. The volume of the top phase was 4.9 mL and the concentrations of butanol, acetone and ethanol were higher in the top phase. Contrarily, the concentration of the salt was higher in the bottom phase and the volume of the bottom phase was 4.5 mL. The distribution coefficients of butanol, acetone and ethanol were 55.70, 30.34 and 8.56, respectively. The recovery yields of butanol and ethanol were 98.38% and 90.31%, respectively.

Example 4

Salting-Out Extraction of Acetone and Butanol from the Simulated Fermentation Broth Using a $Na_2CO_3$/Ethanol System $Na_2CO_3$ (1.5 g) was added to 6 g of the simulated fermentation broth. Then, after the salt was dissolved, 2.5 g ethanol (95%) was added. The resultant mixture was mixed and then held. Two phases were formed. The volume of the top phase was 5.1 mL and the concentrations of butanol, acetone and ethanol were higher in the top phase. Contrarily, the concentration of the salt was higher in the bottom phase and the volume of the bottom phase was 3.9 mL. The distribution coefficients of butanol, acetone and ethanol were 35.06, 65.96 and 13.82, respectively. The recovery yields of butanol and acetone were 97.87% and 98.85%, respectively.

Example 5

Salting-Out Extraction of Butanol and Ethanol from the Fermentation Broth Using a $K_2HPO_4$/Acetone System $K_2HPO_4$ (3 g) was added to 5 g of the fermentation broth. Then, after the salt was dissolved, 2 g acetone was added. The resultant mixture was mixed and then held. Three phases were formed. The volume of the top phase was 3.5 mL and the concentrations of butanol, acetone and ethanol were higher in the top phase. The middle phase mainly consisted of cells and proteins, and its volume was 0.7 mL. The concentration of the salt was higher in the bottom phase and the volume of the bottom phase was 5 mL. The removal ratios for the proteins and cells were 91.21% and 99.86%, respectively. The distribution coefficients of acetone and ethanol were 67.58 and 24.51, respectively. The recovery yield of ethanol was 94.49%. Almost all the butanol was concentrated in the top phase and none was detected in the bottom phase.

Example 6

Salting-Out Extraction of Butanol and Ethanol from the Fermentation Broth Using a $Na_2CO_3$/Acetone System $Na_2CO_3$ (1.8 g) was added to 6 g of the fermentation broth. Then, after the salt was dissolved, 2 g acetone was added. The resultant mixture was mixed and then held. Three phases were formed. The volume of the top phase was 3.8 mL and the concentrations of butanol, acetone and ethanol were higher in the top phase. The middle phase mainly consisted of cells and proteins, and its volume was 0.7 mL. The concentration of the salt was higher in the bottom phase and the volume of the bottom phase was 5.1 mL. The removal ratios for the proteins and cells were 87.13% and 99.92%, respectively. The distribution coefficients of butanol, acetone and ethanol were 32.17, 35.79 and 2.59, respectively. The recovery yields of butanol and ethanol was 95.99% and 91.21%, respectively.

The invention claimed is:
1. A method for salting-out extraction of acetone and butanol from a fermentation broth, characterized in that salts and extractants are added to an acetone-butanol-ethanol (ABE) fermentation broth; the salt saturation achieves

10%~100% in the fermentation broth after addition of the salts; the extractants are alcohols or ketones; and the volume ratio of the fermentation broth containing salts to the extractants is 1:0.1~1:5.

2. The method of claim 1, wherein the fermentation broth is an untreated fermentation broth containing bacteria, an untreated concentrated broth containing bacteria, a bacteria-removed clear broth, or a bacteria-removed concentrated broth; and the concentration of acetone and butanol is 4-500 g/L in the fermentation broth.

3. The method of claim 1, characterized in that the salts are one type, or two or more types of salts.

4. The method of claim 1, characterized in that the extractants are one type, or two or more types of extractants.

5. The method of claim 3, characterized in that the salts are sodium carbonate, potassium carbonate, sodium chloride, lithium chloride, ammonium sulphate, sodium sulphate, dipotassium hydrogen phosphate, sodium hydrogen phosphate, potassium phosphate, sodium phosphate, potassium dihydrogen phosphate, sodium dihydrogen phosphate, sodium acetate, potassium acetate, sodium citrate, potassium citrate, sodium oxalate or potassium oxalate.

6. The method of claim 4, characterized in that the extractants are methanol, ethanol, acetone, n-propanol, isopropanol, n-butanol, isobutanol, ethylene glycol, ether, methyl acetate or ethyl acetate.

7. The method of claim 1, characterized in that the salting-out extraction is conducted in a batch or continuous operation mode; and a multistage extraction mode is applied in the system with a lower distribution coefficient.

8. The method of claim 3, characterized in that the salts are solid or concentrated salt solutions.

* * * * *